United States Patent
Kusaka et al.

(10) Patent No.: US 10,227,456 B2
(45) Date of Patent: Mar. 12, 2019

(54) HIGH-RECOVERABILITY RESIN PARTICLES OF A CROSSLINKED (METH)ACRYLIC ACID ESTER-BASED RESIN, AND USE THEREOF

(71) Applicant: SEKISUI PLASTICS CO., LTD., Osaka (JP)

(72) Inventors: Akiyoshi Kusaka, Nara (JP); Kaori Kuwagaki, Nara (JP); Ryosuke Harada, Shiga (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 5 days.

(21) Appl. No.: 15/509,231

(22) PCT Filed: Sep. 9, 2015

(86) PCT No.: PCT/JP2015/075532
§ 371 (c)(1),
(2) Date: Mar. 7, 2017

(87) PCT Pub. No.: WO2016/039357
PCT Pub. Date: Mar. 17, 2016

(65) Prior Publication Data
US 2017/0260342 A1 Sep. 14, 2017

(30) Foreign Application Priority Data

Sep. 11, 2014 (JP) .................................. 2014-185255

(51) Int. Cl.

| | | |
|---|---|---|
| *C08G 18/10* | (2006.01) | |
| *C08J 3/24* | (2006.01) | |
| *C09D 7/40* | (2018.01) | |
| *A61Q 1/12* | (2006.01) | |
| *A61K 8/81* | (2006.01) | |
| *A61Q 19/00* | (2006.01) | |
| *C08F 2/18* | (2006.01) | |
| *C08F 2/44* | (2006.01) | |
| *C08F 290/06* | (2006.01) | |
| *C08F 299/06* | (2006.01) | |
| *C09D 201/00* | (2006.01) | |
| *C08L 55/00* | (2006.01) | |
| *A61K 8/06* | (2006.01) | |
| *A61K 8/87* | (2006.01) | |
| *A61Q 1/02* | (2006.01) | |
| *C08G 18/32* | (2006.01) | |
| *C08G 18/34* | (2006.01) | |
| *C08G 18/44* | (2006.01) | |
| *C08G 18/48* | (2006.01) | |
| *C08G 18/66* | (2006.01) | |
| *C08G 18/73* | (2006.01) | |
| *C08G 18/78* | (2006.01) | |
| *C08G 18/83* | (2006.01) | |
| *C08K 3/36* | (2006.01) | |
| *C09D 175/16* | (2006.01) | |
| *C08G 18/67* | (2006.01) | |
| *C08G 18/80* | (2006.01) | |

(52) U.S. Cl.
CPC ........ *C08J 3/24* (2013.01); *A61K 8/06* (2013.01); *A61K 8/81* (2013.01); *A61K 8/87* (2013.01); *A61Q 1/02* (2013.01); *A61Q 1/12* (2013.01); *A61Q 19/00* (2013.01); *C08F 2/18* (2013.01); *C08F 2/44* (2013.01); *C08F 290/06* (2013.01); *C08F 299/06* (2013.01); *C08G 18/10* (2013.01); *C08G 18/3221* (2013.01); *C08G 18/348* (2013.01); *C08G 18/44* (2013.01); *C08G 18/4829* (2013.01); *C08G 18/664* (2013.01); *C08G 18/6607* (2013.01); *C08G 18/672* (2013.01); *C08G 18/6725* (2013.01); *C08G 18/73* (2013.01); *C08G 18/7837* (2013.01); *C08G 18/8016* (2013.01); *C08G 18/8025* (2013.01); *C08G 18/831* (2013.01); *C08K 3/36* (2013.01); *C08L 55/00* (2013.01); *C09D 7/40* (2018.01); *C09D 175/16* (2013.01); *C09D 201/00* (2013.01); *A61K 2800/412* (2013.01); *C08J 2375/16* (2013.01)

(58) Field of Classification Search
CPC ......... C08G 18/09; C08G 18/10; C08G 18/34
See application file for complete search history.

(56) References Cited

U.S. PATENT DOCUMENTS

| 2005/0266057 | A1* | 12/2005 | Hagura | .................. A61K 8/02 424/443 |
|---|---|---|---|---|
| 2015/0291725 | A1 | 10/2015 | Nakamura et al. | |

FOREIGN PATENT DOCUMENTS

| CN | 103304767 | 9/2013 |
|---|---|---|
| JP | 2010-202707 | 9/2010 |
| JP | 2011-184544 | 9/2011 |
| JP | 2012-197436 | 10/2012 |
| JP | 2013-82924 | 5/2013 |

(Continued)

OTHER PUBLICATIONS

Machine Translation JP 2010-215,764 (2010) (Year: 2010).*
International Search Report dated Dec. 8, 2015 in International Application No. PCT/JP2015/075532.

*Primary Examiner* — Hoa (Holly) Le
(74) *Attorney, Agent, or Firm* — Wenderoth, Lind & Ponack, L.L.P.

(57) ABSTRACT

A high-recoverability resin particles having a mean particle size of 1 to 100 μm containing a cross-linked (meth)acrylic acid ester-based resin, wherein the high-recoverability resin particles have a recovery rate of 22% or greater, and a 30% compression strength of 1.5 to 5.0 kgf/mm².

11 Claims, No Drawings

(56) References Cited

FOREIGN PATENT DOCUMENTS

| JP | 5297845 | 9/2013 |
|----|---------|--------|
| JP | 2014-105263 | 6/2014 |
| JP | 2014-122338 | 7/2014 |
| JP | 2014-133860 | 7/2014 |

* cited by examiner

HIGH-RECOVERABILITY RESIN PARTICLES OF A CROSSLINKED (METH)ACRYLIC ACID ESTER-BASED RESIN, AND USE THEREOF

TECHNICAL FIELD

The present invention relates to a high-recoverability resin particles and use thereof. More particularly, the present invention relates to the high-recoverability resin particles useful for an application which intends to form a coating film such as a self repairing coating composition or cosmetics, and a coating composition and cosmetics containing the particle.

BACKGROUND ART

Some interior components for automobiles have been made with matte paint finish. Such matte paint finish has been carried out with a matting agent that is a coating composition supplemented with a pigment for gloss control represented by silica and talc. However, a coating film obtained by using the above-described matting agent have problems that the film feels hard to the touch, and that the film is prone to be scratched by an external impact. Accordingly, the coating film having high scratch resistance, soft feel (soft feel property), smooth feel and high elasticity is required. The coating film having such properties is also required for cosmetics.

As a method for imparting a unique pattern and soft feel to the coating film, and improving scratch resistance of the coating film, generally known methods include a method adding a slipping agent, such as acrylic resin particles, urethane resin particles, nylon resin particles, silicone resin particles and polyethylene resin particles, to a coating composition.

For example, Japanese Patent No. 5297845 (Patent Document 1) provides resin particles which can form the coating film having an excellent recovery rate, and having soft feel to the touch with excellent, scratch resistance obtained by polymerization of a mixture containing a specific cross-linkable monomer having vinyl groups at the both ends of the molecule and a (meth)acrylic acid ester.

PRIOR ART DOCUMENTS

Patent Documents

Patent Document 1: Japanese Patent No. 5297845

SUMMARY OF THE INVENTION

Problems to be Solved by the Invention

However, the above-described prior art is still not sufficient, and thus it is required to provide resin particles, which can be used in a coating film, having further improved properties (especially, a high recovery rate).

Solution to the Problems

Accordingly, the present invention provides a high recoverability resin particles having a mean particle size of 1 to 100 μm containing a cross-linked (meth)acrylic acid ester-based resin, wherein the high-recoverability resin particles have a recovery rate of 22% or greater, and a 30% compression strength of 1.5 to 5.0 kgf/mm$^2$.

Further, the present invention provides a coating composition containing the above-described high-recoverability resin particles.

Furthermore, the present invention provides a coating film obtained by applying and drying the above-described coating composition.

Moreover, the present invention provides cosmetics containing the high-recoverability resin particles.

Effects of the Invention

Resin particles having high recoverability can be provided by the present invention. By using the resin particles in a coating film, or cosmetics, high scratch resistance or soft feel to the touch or soft feel in use can be imparted to the coating film or cosmetics.

Further, resin particles having higher recoverability can be provided in any one of the following conditions:
(1) When the cross-linked (meth)acrylic acid ester-based resin contains a resin derived from a crosslinkable oligomer having two or more radical-polymerizable groups obtained by reacting (a) polyol, (b) polyisocyanate and (c) (meth)acrylic acid esters having an OH group, and a (meth)acrylic acid ester-based monofunctional monomer,
wherein the cross-linked (meth)acrylic acid ester-based resin shows Tg of 0 to 30° C. (determined from viscoelasticity) when the crosslinkable oligomer is cured alone,
(2) When the high-recoverability resin particles are, a polymerization product of a monomer mixture obtained by polymerization of the monomer mixture containing 20 to 80 mass % of a (meth)acrylic acid ester-based monofunctional monomer and 80 to 20 mass % of a crosslinkable oligomer, wherein the (meth)acrylic acid ester-based monofunctional monomer is a (meth)acrylic acid ester of an alcohol having 1 to 8 carbon atoms,
(3) When the cross-linked (meth)acrylic acid ester-based resin contains of a resin formulation showing a hysteresis loss of 30% or less.

EMBODIMENTS OF THE INVENTION (High-Recoverability Resin Particles)

High-recoverability resin particles are a resin particle having a mean particle size of 1 to 100 μm containing a cross-linked (meth)acrylic acid ester-based resin. Resin particles having a mean particle size within the above range can further improve recoverability and a matte effect when used in a coating film. When the mean particle size is smaller than 1 μm, since irregularities formed in the coating film can be small, a substantial matte effect can not always be obtained. On the other hand, when the mean particle size of the particle is greater than 100 μm, the coating film can be rough and bumpy, and thus the appearance can be unattractive. A preferable mean particle size is 1 to 80 μm, and a more preferable mean particle size is 1 to 50 μm. The mean particle size can be 1 μm, 5 μm, 10 μm, 20 μm, 30 μm, 40 μm, 50 μm, 60 μm, 70 μm, 80 μm, 90 μm and 100 μm.

The high-recoverability resin particles have a recovery rate of 22% or more. When the high-recoverability resin particle has the recovery rate of 22% or more, the coating film having high recoverability can be obtained. When the recovery rate is smaller than 22%, the coating film having high recoverability can not always be obtained. A preferable recovery rate is 25% or more, and more preferable recovery rate is 30% or more. An upper limit of the recovery rate is 100%. The recovery rate can be 22%, 30%, 40%, 50%, 60%, 70%, 80%, 90% and 100%.

The high-recoverability resin particles have a 30% compression strength of 1.5 to 5.0 kgf/mm$^2$, When particles having the compression strength within the above range are used in the coating film, soft feel can be obtained. Further, disintegration of particles by kneading during production of a coating composition can be reduced. When the 30% compression strength is smaller than 1.5 kgf/mm$^2$, particles can be disintegrated by kneading during production of the coating composition. When the 30% compression strength is greater than 5.0 kgf/mm$^2$, the coating film can be hard to the touch. A preferable 30% compression strength is 1.8 to 4.5 kgf/mm$^2$, and a more preferable 30% compression strength is 2.0 to 4.0 kgf/mm$^2$. The 30% compression strength can be 1.5 kgf/mm$^2$, 1.8 kgf/mm$^2$, 2.0 kgf/mm$^2$, 2.5 kgf/mm$^2$, 3.0 kgf/mm$^2$, 3.5 kgf/mm$^2$, 4.0 kgf/mm$^2$, 4.5 kgf/mm$^2$ and 5.0 kgf/mm$^2$.

A constituting ingredient of the high-recoverability resin particles is not specifically limited, provided that the particles have the mean particle size, the recovery rate and the 30% compression strength within the above ranges. A resin derived from a crosslinkable oligomer having two or more radical-polymerizable groups and a (meth)acrylic acid ester-based monofunctional monomer can be used.

The high-recoverability resin particles contain preferably a resin formulation showing a hysteresis loss of 30% or less. The resin formulation showing the hysteresis loss of 30% or less makes it possible to obtain the coating film having high trackability against compression displacement by a load or the like, and having high scratch resistance. When the hysteresis loss is greater than 30%, the coating film having high recoverability can not always be obtained. A preferable hysteresis loss is 25% or less, and a more preferable hysteresis loss is 20% or less. A lower limit of the hysteresis loss is 0%. The hysteresis loss can be 0%, 5%. 10%, 15%, 20%, 25% and 30%.

(1) Crosslinkable Oligomer

The crosslinkable oligomer is preferably, for example, an urethane meth)acrylate obtained by a reaction of (a) polyol, (b) polyisocyanate and (c) a (meth)acrylic acid ester having an OH group. When the cross-linked (meth)acrylic acid ester-based resin is a crosslinked resin derived from the urethane (meth)acrylate, high-recoverability resin particles can be obtained.

Further, the components (a) to (c) are preferably selected from components which can impart Tg of 0 to 30° C. (determined from viscoelasticity) to a resin formed by curing a crosslinkable oligomer alone. When Tg is lower than 0° C., the crosslinked resin can sometimes be sticky. When Tg is greater than 30° C., resin particles having high recoverability can not always be obtained. More preferable Tg is 0 to 28° C., and further more preferable Tg is 0 to 25° C. Tg can be 0° C., 5° C., 10° C., 15° C., 20° C., 28° C. and 30° C.

Furthermore, the crosslinkable oligomer preferably shows a (meth)acrylic equivalent of 300 to 1000 g/mol. When the (meth)acrylic equivalent is smaller than 300 g/mol, sufficient flexibility can not always be obtained. When the (meth)acrylic equivalent is greater than 1000 g/mol, sufficient flexibility can not always be obtained. A more preferable (meth)acrylic equivalent is 350 to 800 g/mol, and a further more preferable (meth)acrylic equivalent is 400 to 600 g/mol. The (meth)acrylic equivalent can be 300 g/mol, 350 g/mol, 400 g/mol, 500 g/mol, 600 g/mol, 700 g/mol, 800 g/mol, 900 g/mol and 1000 g/mol. The (meth)acrylic equivalent is a calculated value (g/mol) of weight of an active energy ray-curable resin(crosslinkable oligomer) containing 1 mole of a (meth)acryloyl group. Specifically, the (meth) acrylic equivalent can be calculated as follows. (Meth)acrylic equivalent (mass of isocyanate adduct component containing component (a) and component (b) (gram)+mass of component (c) (gram))/number of moles of component (c)

(a) Polyols

Examples of the polyol include a polyester-based polyol, a polyether-based polyol, a polycarbonate polyol, an aliphatic hydrocarbon-based polyol and an alicyclic hydrocarbon-based polyol.

Any one of the polyols listed above may be used alone, or two or more of the polyols may be used in combination.

The polyol has preferably a number average molecular weight of 200 to 3000 and 2 to 4 OH groups. When the number average molecular weight is less than 200 or greater, than 3000, the crosslinked resin can be excessively hard, and resin particles having high recoverability can not always be obtained. When the polyol has fewer than 2 OH groups, crosslinkability can be excessively low. When the polyol has more than 4 OH groups, crosslinkability can be excessively high, and resin particles having high recoverability can not always be obtained. The number average molecular weight can be 200, 500, 1000, 1500, 2000, 2500 and 3000.

(a-1) Examples of the polyester-based polyol include a condensation polymerization product of a polyalcohol and a polycarboxylic acid; a ring-opening polymerization product of a cyclic ester (lactone); and a reaction product of the following 3 components: a polyalcohol, polycarboxylic acid and a cyclic ester; or the like, wherein each component is selected so that 3 or more hydroxy groups are included in the reaction product.

Examples of the polyalcohol described above include ethylene glycol, diethylene glycol, propylene glycol, dipropylene glycol, trimethylene glycol, 1,4-tetramethylenediol, 1,3-tetramethylenediol, 2-methyl-1,3-trimethylenediol, 1,5-pentamethylenediol, neopentylglycol, 1,6-hexamethylenediol, 3-methyl-1,5-pentamethylenediol, 2,4-diethyl-1,5-pentamethylenediol, methantriol, glycerin, trimethylolpropane, trimethylolethane, 1,2,6-hexane triol, pentaerythritol, cyclohexanediols (e.g., 1,4-cyclohexanediol), bisphenols (e.g., bisphenol A) and sugar alcohols (e.g., xylitol and sorbitol).

Examples of the polycarboxylic acid described above include an aliphatic dicarboxylic acid such as malonic acid, maleic acid, fumaric acid, succinic add, glutaric acid, adipic acid, suberic acid, azelaic acid, sebacic acid, dodecanedioic acid; an alicyclic dicarboxylic acid such as 1,4-cyclohexanedicarboxylic acid; and an aromatic dicarboxylic acid such as terephthalic acid, isophthalic acid, orthophthalic acid, 2,6-naphthalene dicarboxylic acid, p-phenylene dicarboxylic acid, trimellitic acid.

Examples of the cyclic ester (lactone) described above include γ-butyrolactone, δ-valerolactone and ε-caprolactone.

(a-2) Examples of the polyether-based polyol described above include a polyether-based polyol obtained by dehydration condensation of a raw material polyalcohol so that 3 or more hydroxy groups are included in an end of the molecule (side chain).

Examples of the polyol include a 3 or more functional polyol, such as a low molecular weight polyol such as methantriol, glycerin, trimethylolpropane, trimethylolethane, 1,2,6-hexane triol and pentaerythritol, and a polyoxyalkylene polyol which is an alkylene oxide adduct of the polyol listed above.

(a-3) Examples of the polycarbonate-based polyol described above include a reaction product of a polyalcohol and phosgene, wherein the polyalcohol is selected so that 3 or more hydroxy groups are contained; and a ring-opening polymerization product of a cyclic carbonic acid ester (e.g., an alkylene carbonate) containing 3 or more hydroxy groups.

Examples of the polyalcohol include a low molecular weigh (preferably molecular weight of 64 to 250) polyalcohol such as methantriol, glycerin, trimethylolpropane, trimethylolethane, 1,2,6-hexane triol and pentaerythritol, and a 3 or more functional polyalcohol such as a polyoxyalkylene polyalcohol which is an alkylene oxide adduct of the polyalcohol listed above.

The polycarbonate-based polyol can be any compound so long as a carbonate bond is contained in the molecule and 3 or more hydroxyl groups are included in an end of the molecule, and can contain an ester bond as well as a carbonate bond.

(a-4) The polyolefin-based polyol described above can be any one having 3 or more hydroxy groups in total in an end of the molecule (side chain) of the hydrocarbon backbone which has at least one branched structure.

(a-5) The hydrogenated polybutadiene-based polyol described above can be any one having a structure wherein all of ethylenically unsaturated groups contained in a structure of the polybutadiene-based polyol are hydrogenated, and having 3 or more hydroxy groups in total in an end of the molecule (side chain).

(b) Polyisocyanates

Examples of the polyisocyanate include an aliphatic polyisocyanate, an alicyclic polyisocyanate, an aromatic polyisocyanate and an aromatic-aliphatic polyisocyanate.

The polyisocyanate contains preferably 2 to 4 NCO groups. When the polyisocyanate has fewer than 2 NCO groups, crosslinkability can be excessively low. When the polyol has more than 4 NCO groups, crosslinkability can be excessively high, and resin particles having high recoverability can not always be obtained.

Examples of the aliphatic polyisocyanate include tetramethylene diisocyanate, dodecamethylene diisocyanate, hexamethylene diisocyanate, 2,2,4-trimethylhexamethylene diisocyanate, 2,4,4-trimethylhexamethylene diisocyanate, lysine diisocyanate, 2-methylpentane-1,5-diisocyanate and 3-methylpentane-1,5-diisocyanate.

Examples of the alicyclic polyisocyanate include isophorone diisocyanate, hydrogenated xylylene diisocyanate, 4,4'-dicyclohexylmethane diisocyanate, 1,4-cyclohexane diisocyanate, methylcyclohexylene diisocyanate and 1,3-bis (isocyanate methyl)cyclohexane.

Examples of the aromatic polyisocyanate include tolylene diisocyanate, 2,2'-diphenylmethane diisocyanate, 2,4'-diphenylmethane diisocyanate, 4,4'-diphenylmethane diisocyanate (MDI), 4,4'-dibenzyl diisocyanate, 1,5-naphthylene diisocyanate, xylylene diisocyanate, 1,3-phenylene diisocyanate and 1,4-phenylene diisocyanate.

Examples of the aromatic-aliphatic polyisocyanate include dialkyldiphenylmethane diisocyanate, tetraalkyl diphenylmethane diisocyanate and α,α,α,α-tetramethylxylylene diisocyanate. Examples of the aromatic-aliphatic polyisocyanate also include a dimer or a trimer of the organic polyisocyanate and a modified substance of the organic polyisocyanate such as biuretized isocyanate.

Any one of the polyisocyanates listed above may be used alone, or two or more of the polyisocyanates may be used in combination.

(c) (Meth)Acrylic Acid Esters Having OH Group

Examples of the (meth)acrylic acid ester having OH group include a (meth)acrylic acid ester of an alcohol having 1 to 8 carbon atoms having an OH group such as 2-hydroxyethyl acrylate, 2-hydroxyethyl methacrylate, 2-hydroxy propyl acrylate 2-hydroxy propyl methacrylate, 4-hydroxy butyl acrylate and caprolactone modified-2-hydroxyethyl acrylate, polyethylene glycol mono(meth)acrylic acid ester, polypropylene glycol monoacrylic acid ester, polybutylene glycol mono(meth)acrylic acid ester, 2-(meth)acryloyloxyethyl-2-hydroxyethyl phthalate phenylglycidyl ether (meth) acrylate, pentaerythritol triacrylate, dipentaerythritol pentaacrylate and caprolactone-modified dipentaerythritol penta (meth)acrylate.

Any one of the (meth)acrylic acid esters having an OH group listed above may be used alone, or two or more of the (meth)acrylic acid esters having an OH group may be used in combination.

Among other (meth)acrylic acid esters having an OH group, the (meth)acrylic acid ester of are alcohol having 1 to 8 carbon atoms having an OH group, and pentaerythritol triacrylate are preferable. Examples of the alcohol having 1 to 8 carbon atoms include methanol, ethanol, propanol, butanol, pentanol, hexanol, heptanol and octanol. The alcohols listed above include their structural isomers.

The (meth)acrylic acid ester having an OH group is preferably a (meth)acrylic acid ester of an alcohol having 1 to 8 carbon atoms for the purpose of obtaining the coating film having higher recoverability. Among others, 2-hydroxyethyl acrylate and 2-hydroxy propyl acrylate are preferably used.

(d) Method for Producing Crosslinkable Oligomers

The crosslinkable oligomer having two or more radical-polymerizable groups can be produced by a well-known method. Examples of the method include the following method. Initially, a predetermined amount of the component (b) is added to a large excess amount of the component (a), and then a reaction is carried out at 90° C. until an amount of free isocyanate reaches a predetermined level. From the obtained reaction mixture, polyurethane is obtained by thin-film distillation under conditions of at 130° C. and 0.04 kPa. Subsequently, to the polyurethane can be added the component (c) at a temperature range of from 70 to 80° C. (preferably under the presence of a polymerization inhibitor such as hydroquinone monomethyl ether), and then the mixture can be agitated at the same temperature until free isocyanate can not be substantially detected to produce a crosslinkable oligomer. Moreover, a tin-based catalyst such as dibutyltin dilaurate can also be added to accelerate the reaction.

The ratio of the component (c) to the component (b) the component (a) is preferably from 1.0 to 2.0 (molar ratio), more preferably from 1.0 to 1.5 (molar ratio). The ratio of the component (c) can be 1.0, 1.2, 1.4, 1.5, 1.7, 1.9 and 2.0.

(f) Other Components

The cross-linked (meth)acrylic acid ester-based resin can contain a component derived from other monomers. The component can be included by making it coexist with the crosslinkable oligomer during polymerization.

Examples of the other monomers include 2-ethylhexyl (meth)acrylate, styrene, methyl methacrylate, acryloyl morpholine, tetrahydrofurfuryl (meth)acrylate, phenoxy ethyl (meth)acrylate, phenoxy propyl (meth)acrylate, benzyl (meth)acrylate, polyethoxyphenyl (meth)acrylate, polyethoxyphenyl (meth)acrylate, phenylbenzyl (meth)acrylate, o-phenylphenol (meth)acrylate, o-phenyl phenoxy ethoxy (meth)acrylate, polyethoxy o-phenyl phenoxy ethoxy (meth) acrylate, isoboronyl (meth)acrylate, cyclohexyl (meth)acrylate, dicyclopentanyl (meth)acrylate, dicyclopentenyl (meth)acrylate, dicyclopentenyloxyethyl (meth)acrylate, phthalic acid mono hydroxyethyl (meth)acrylate, ethylene glycol di(meth)acrylate, propylene glycol di(meth)acrylate, polyethylene glycol di(meth)acrylate, polypropylene glycol di(meth)acrylate, polytetramethylene di(meth)acrylate, 1,4-butanediol-di(meth)acrylate, 1,6-hexanediol-di(meth)acrylate, 1,9-nonanediol di(meth)acrylate EO (ethylene oxide, the same applies below) modified bisphenol di(meth)acrylate, PO (propylene oxide, the same applies below) modified bisphenol di(meth)acrylate, dimethylol dicyclopentane di(meth)acrylate, neopentylglcol di(meth)acrylate, neopentylglycol di(meth)acrylate, trimethylolpropane tri(meth)acrylate, EO-modified trimethylolpropane tri(meth)acrylate, PO-modified trimethylolpropane tri(meth)acrylate, pentaerythritol tri(meth)acrylate, ((meth) acryloxyethyl)isocyanurate, pentaerythritol tetra(meth)acrylate, EO-modified pentaerythritol tetra(meth)acrylate PO-modified pentaerythritol tetra(meth)acrylate, ditrimethylolpropane tetra(meth)acrylate, EO-modified ditrimethylolpropane tetra(meth)acrylate, PO-modified ditrimethylolpropane tetra(meth)acrylate dipentaerythritol hexa(meth)acrylate, EO-modified dipentaerythritol hexa(meth)acrylate, PO-modified dipentaerythritol hexa(meth)acrylate, caprolactone-modified dipentaerythritol hexa(meth)acrylate and dipentaerythritol penta(meth)acrylate. Any one of the monomers listed above may be used alone, or two or more of the monomers may be used in combination.

(2) Method for Producing High-Recoverability Resin Particles

The high-recoverability resin particles can be obtained by dissolving the crosslinkable oligomer in a monomer to give an oil phase, and then carrying out suspension polymerization of the obtained oil phase in an aqueous medium.

The monomer used is preferably, but not specifically limited to, a (meth)acrylic acid ester-based monofunctional monomer of an alcohol having 1 to 8 carbon atoms. Specifically, the monomers include the monomer having no OH group such as methyl (meth)acrylate, ethyl (meth)acrylate, propyl (meth)acrylate, butyl (meth)acrylate and pentyl (meth)acrylate. Any one of the monomers listed above may be used alone, or two or more of the monomers may be used in combination.

Ratios of the (meth)acrylic acid ester-based monofunctional monomer used and the crosslinkable oligomer used are preferably 20 to 80 mass % and 80 to 20 mass %, respectively. When the ratio of the (meth)acrylic acid ester-based monofunctional monomer used is less than 20 mass %, sufficient flexibility can not always be obtained. When the ratio is greater than 80 mass %, resin particles having high recoverability can not always be obtained. A preferable ratio of the (meth)acrylic acid ester-based monofunctional monomer used is 40 to 80 mass %, and a more preferable ratio of the (meth)acrylic acid ester-based monofunctional monomer used is 45 to 75 mass %. A ratio of the (meth)acrylic acid ester-based monofunctional monomer used can be 20 mass %, 30 mass %, 40 mass %, 45 mass %, 50 mass %, 60 mass %, 70 mass %, 75 mass % and 80 mass %.

For suspension polymerization, a radical polymerization initiator is used, if necessary.

Examples of the radical polymerization initiator include an oil-soluble peroxide such as benzoyl peroxide, lauroyl peroxide, octanoyl peroxide, o-chloro benzoyl peroxide, methyl ethyl ketone peroxide, diisopropyl peroxydicarbonate, cumene hydroperoxide and t-butyl hydroperoxide, and an oil-soluble azo compound such as 2,2'-azobisisobutyronitrile and 2,2'-azobis(2,4-dimethylvaleronitrile).

Any one of the polymerization initiators listed above may be used alone, or two or more of the polymerization initiators may be used in combination. A sufficient ratio of the polymerization initiator used per 100 parts by mass in total of the crosslinkable oligomer and the (meth)acrylic acid ester used is on the order of 0.1 to 1 parts by mass.

For suspension polymerization, a dispersant and/or a surfactant can also be used.

As the dispersant, a suspending-dispersing agent, which can generally be used, for example, a poor water-soluble inorganic salt such, as calcium phosphate, magnesium pyrophosphate and colloidal silica, and a water-soluble polymer such as polyvinyl alcohol, methyl cellulose and polyvinyl pyrrolidone can be used.

Examples of the surfactant include water-soluble surfactants, for example, an anionic surfactant such as sodium oleate, sodium lauryl sulfate, sodium dodecylbenzenesulfonate, alkylnaphthalene sulfonate and an alkyl phosphoric acid ester salt, a nonionic surfactant such as polyoxyethylene alkyl ether, a polyoxyethylene alkyl phenyl ether, a polyoxyethylene fatty acid ester, a sorbitan fatty acid ester, a polyoxysorbitan fatty acid ester, a polyoxyethylene alkylamine and a glycerine fatty acid ester, and an amphoteric surfactant such as lauryldimethylamine oxide. Further, examples of the surfactant include oil-soluble surfactants, for example, caprolactone EO-modified dimethacrylate phosphate, mono-isodecyl phosphate, 2-ethylhexyl acid phosphate and isodecyl acid phosphate.

Any one of the dispersants and the surfactants listed above may be used alone, or two or more of the dispersants and the surfactants may be used in combination. Among others, the dispersant of the poor water-soluble phosphoric acid salt such as calcium phosphate and magnesium pyrophosphate, and the anionic surfactant such as an alkyl sulfuric acid salt and an alkyl benzenesulfonic acid salt are preferably used in combination for the purpose of dispersion stability.

A ratio of the dispersant used per 100 parts by mass in total of the monomer for the cross-linked (meth)acrylic acid ester-based resin is on the order of 0.5 to 10 parts by mass, and a ratio of the surfactant used per 100 parts by mass of an aqueous medium used is on the order of 0.01 to 0.2 mass %.

A polymerization reaction can be initiated by mixing the oil phase (e.g., the monomer, the polymerization initiator, the non-polymerizable organic solvent) and an aqueous phase (e.g., the aqueous medium, the dispersant, the surfactant), and then elevating the temperature under agitation. An amount of the aqueous phase used is preferably 100 to 1000 parts by mass per 100 parts by mass of the oil phase. Examples of the aqueous media include water, and a mixture of water and a water-soluble organic solvent (e.g., a lower alcohol).

A polymerization temperature is preferably on the order of 40 to 90° C. A time of polymerization, while a reaction system is kept at polymerization temperature, is generally on the order of 1 to 10 hours. A mean particle size of a resin particle can suitably be controlled by regulating mixing ratio between an oil phase and an aqueous phase, an amount of the dispersant and the surfactant used, agitation conditions and dispersion conditions.

Examples of a method for dispersing the oil phase in the aqueous phase as fine droplets include a method using an agitation force of propeller blade or the like, a method using a homogenizer, a method using an emulsifying disperser utilizing a high shear force exerted at a gap between a rotary vane and a wall of the disperser or between rotary vanes, a method using an ultrasonication disperser, and a method using a high-pressure jet disperser. In case of using the homogenizer, for example, when a rotation rate is high and dispersing time is long, a resultant droplet diameter tends to be small.

After completion of the polymerization reaction, the dispersant is decomposed and removed by an acid or the like, if desired, and then filtration, wash with water, dehydration, drying, pulverizing and sizing are carried out to obtain desired resin particles.

(Coating Composition)

The high-recoverability resin particles have the specific compression strength, recovery rate and hysteresis loss, and thus softness and/or matting properties can be imparted to the coating film obtained from a coating composition containing the high-recoverability resin particles.

The coating composition contains a binder resin or a solvent, if desired. Examples of the binder resin used include an organic solvent-soluble resin or a water-soluble resin, or a water-dispersible and emulsion type aqueous resin.

Examples of the binder resin include an acrylic resin, an alkyd resin, a polyester resin, a polyurethane resin, a chlorination polyolefin resin and an amorphous polyolefin resin. The binder resin listed above can appropriately be selected according to adherence of a paint to a substrate to be painted or an environment of use.

Amounts of the binder resin and the high-recoverability resin particles added can vary depending, among other things, on a film thickness of the coating film to be formed, a mean particle size of the high-recoverability resin particles, and a coating method. An amount of the binder resin added is preferably 5 to 50 mass % of the sum of the binder resin (solid contents when an emulsion-type aqueous resin is used) and the high-recoverability resin particles. When the content of the high-recoverability resin particles is less than 5 mass %, a sufficient matte effect can not always be obtained. When the content is greater than 50 mass %, a viscosity of the coating composition can be excessively high, which can result in improper dispersion of the high-recoverability resin particles. As a result, the obtained coating film can have defective appearance, for example, microcracks formed on the coating film or rough surface formed on the coating film, and thus the content described above is not preferable. A more preferable content is 10 to 50 mass %, and a further more preferable content is 20 to 40 mass %.

The solvent used is preferably, but not specifically limited to, the solvent which can dissolve or disperse the binder resin. Examples of the solvent for oil-based paints include a hydrocarbon-based solvent such as toluene and xylene; a ketone-based solvent such as methyl ethyl ketone and methyl isobutyl ketone; an ester-based solvent such as ethyl acetate and butyl acetate; an ether-based solvent such as dioxane, ethylene glycol diethyl ether and ethylene glycol monobutyl ether. Examples of the solvent for water-based paints used include water and alcohols. Any one of the solvents listed above may be used alone, or two or more of the solvents may be used in combination. The content of the solvent in the coating composition can be generally on the order of 20 to 60 mass % of the whole paint composition.

The coating composition can contain a well-known coating controlling agent, fluidity controlling agent, ultraviolet absorber, light stabilizer, curing catalyst, extender pigment, coloring pigment, metal pigment, mica powder pigment and dye, if necessary.

A method for forming the coating film using the coating composition is not specifically limited and any well-known method can be used. Examples of the method include a spray painting method, a roller painting method and a brush painting method. The paint composition can be diluted so as to adjust its viscosity as required. Examples of the diluent include a hydrocarbon-based solvent such as toluene and xylene; a ketone-based solvent such as methyl ethyl ketone and methyl isobutyl ketone; an ester-based solvent such as ethyl acetate and butyl acetate; an ether-based solvent such as dioxane and ethylene glycol diethyl ether; water; and an alcohol-based solvent. Any one of the diluents listed above may be used alone, or two or more of the diluents may be used in combination.

(Cosmetics)

Since the high-recoverability resin particles have the specific compression strength, recovery rate and hysteresis loss, cosmetics containing the high-recoverability resin particles have very soft feel to the touch and light feel in use.

The cosmetics contain the high-recoverability resin particles preferably in the range of from 1 to 40 mass %. When the content is less than 1 mass %, the number of the resin particles can be excessively small, and thus obvious effects by the addition can not always be exerted. When the content is greater than 40 mass %, an extra amount added can not always promote notable effects corresponding to the extra amount added.

Examples of the cosmetics include cleaning cosmetics such as soap, body wash, cleansing cream and facial scrub, body cosmetics such as a cosmetic lotion, cream, emulsion, facial packs, facial powders, foundation, lipstick, lip cream, facial rouge, facial cosmetics, manicure cosmetics, hair wash cosmetics, hair dye, hair liquid, fragrant cosmetics, toothpaste, bath salts, antiperspirant, sunblock products, suntan products, body powder and baby powder, shaving cream, and lotions such as pre-shave lotion, after-shave lotion and body lotion.

A component generally used in cosmetics can be compounded as necessary so long as it does not impair the effects of the present invention. Examples of the component described above include water, a lower alcohol, oils, fats and waxes, hydrocarbon, a higher fatty acid, a higher alcohol, a sterol, a fatty acid ester, metallic soap, a humectant, a surfactant, a high molecular compound, coloring raw materials, a flavoring, a preservative and sterilizing agent, an antioxidant, an ultraviolet absorber and a special formulation component.

Examples of the oils, fats and waxes include avocado oil, almond oil, olive oil, cacao butter, beef tallow, sesame oil, wheat-germ oil, safflower oil, shea butter, turtle oil, camellia oil, persic oil, castor oil, grape seed oil, macadamia nut oil, mink oil, egg-yolk oil, sumac wax, palm oil, rose hip oil, hydrogenated oil, silicon oil, orange toughy oil, carnauba wax, candelilla wax, spermaceti wax, jojoba oil, montan wax, beeswax and lanolin.

Examples of the hydrocarbon include a liquid paraffin, petrolatum, paraffin, ceresin, microcrystalline wax and squalane. Examples of the higher fatty acid include lauric acid, mystic acid, palmitic acid, stearic acid, oleic acid, behenic acid, undecylenic acid, oxystearic acid, linoleic acid, a lanolin fatty acid and a synthesis fatty acid.

Examples of the higher alcohol include lauryl alcohol, cetyl alcohol, cetostearyl alcohol, stearyl alcohol, oleyl alcohol, behenyl alcohol, lanolin alcohol, a hydrogenated lanolin alcohol, hexyldecanol, octyldecanol, isostearyl alcohol, jojoba alcohol and decyl tetradecanol.

Examples of the sterol include cholesterol, dihydro cholesterol and phytocholesterol. Examples of the fatty acid ester include ethyl linoleate, isopropyl myristate, lanolin fatty acid isopropyl, hexyl laurate, myristyl myristate, cetyl myristate, octyldodecyl myristate, decyl oleate, octyldodecyl oleate, hexadecyl dimethyloctanoate, cetyl isooctanoate, decyl palmitate, glyceryl trimyristate, tri(caprylic/capric acid)glycerol, propylene glycol dioleate, glyceryl triisostearate, glyceryl triisooctanoate, cetyl lactate, myristyl lactate, diisostearyl malate, and a cyclic alcohol fatty acid ester such as cholesteryl isostearate and cholesteryl 12-hydroxystearate.

Examples of the metallic soap include zinc laurate, zinc myristate, magnesium myristate, zinc palmitate, zinc stearate, aluminum stearate, calcium stearate, magnesium stearate and zinc undecylenate. Examples of the humectant include glycerin, propylene glycol, 1,3-butylene glycol, polyethylene glycol, sodium dl-pyrrolidone carboxylate, sodium lactate, sorbitol, sodium hyaluronate, polyglycerol, xylite and maltitol.

Examples of the surfactant include an anionic surfactant such as a higher fatty acid soap, a higher alcohol sulfate, N-acylglutamic acid salt and a phosphoric acid ester salt, a cationic surfactant such as an amine salt and quaternary ammonium salt, an amphoteric surfactant such as betaine surfactants, amino acid surfactants, imidazoline surfactants and lecithin, and a nonionic surfactant such as a fatty acid monoglyceride, a propylene glycol fatty acid ester, a sorbitan fatty acid ester, a sucrose fatty acid ester, a polyglycerin fatty acid ester and an ethylene oxide condensate.

Examples of the high molecular compound include a natural high molecular compound such as gum arabic, traganth gum, guar gum, locust bean gum, karaya gum, Irish moss, quince seed, gelatin, shellac, rosin and casein, a semi-synthetic high molecular compound such as carboxymethyl cellulose sodium, hydroxyethyl cellulose, methyl cellulose, ethyl cellulose, sodium alginate, ester gum, nitrocellulose, hydroxy propyl cellulose and crystalline cellulose, and a synthetic high molecular compound such as polyvinyl alcohol, polyvinyl pyrrolidone, sodium polyacrylate, a carboxyvinyl polymer, polyvinyl methyl ether, a polyamide resin, a silicone oil and a resin particle such as a nylon particle, a polymethyl methacrylate particle, a cross-linked polystyrene particle, a silicon particle, an urethane particle, a polyethylene particle and a silica particle.

Examples of the coloring raw material include an inorganic pigment such as iron oxide, lapis lazuli, Prussian blue, chromium oxide, chromium hydroxide, carbon black, manganese violet, titanium oxide, zinc oxide, talc, kaolin, mica, carbonate calcium, carbonate magnesium, mica, silicate aluminum, silicate barium, silicate calcium, silicate magnesium, silica, zeolite, barium sulfate, calcined calcium sulfate (exsiccated gypsum), calcium phosphate, hydroxyapatite and a ceramic powder, and a tar dye such as azo-based, nitro-based, nitroso-based, xanthene-based, quinoline-based, anthraquinoline-based, indigo-based, triphenylmethane-based, phthalocyanine-based and pyrene-based dyes.

The powder ingredients such as the above-described high molecular compound and coloring raw material can be surface treated in advance. As a surface treatment method, well-known surface treatment techniques can be used. Examples of the surface treatment method include an all treatment using a hydrocarbon oil, ester oil, lanolin or the like, a silicone treatment using dimethyl polysiloxane, methyl hydrogen polysiloxane, methyl phenyl polysiloxane or the like, a fluorine compound treatment using an ester containing a perfluoroalkyl group, perfluoroalkylsilane perfluoropolyether, a polymer having an perfluoroalkyl group or the like, a silane coupling agent treatment using 3-methacryloxypropyltrimethoxysilane, 3-glycidoxypropyltrimethoxysilane or the like, a titanium coupling agent treatment using isopropyl triisostearoyl titanate, isopropyl tris (dioctyl pyrophosphate)titanate or the like, a metallic soap treatment, an amino acid treatment using acylglutamic acid or the like, a lecithin treatment using hydrogenated egg-yolk lecithin or the like, a collagen treatment, a polyethylene treatment, a moisturizing treatment, an inorganic compound treatment and a mechanochemical treatment.

Examples of the flavoring include a natural flavoring such as lavender oil, peppermint oil and lime oil, and a synthetic flavoring such as ethyl phenyl acetate, geraniol and p-tert-butyl cyclohexyl acetate. Examples of the preservative and sterilizing agent include methylparaben, ethylparaben, propylparaben, benzalkonium and benzethonium.

Examples of the antioxidant include dibutylhydroxytoluene, butyl hydroxyanisole, propyl gallate and tocopherol. Examples of the ultraviolet absorber include inorganic absorbers such as a particulate titanium oxide, a particulate zinc oxide, a particulate cerium oxide, a particulate iron oxide and a particulate zirconium oxide, and organic absorbers such as benzoic acid-based, para-aminobenzoic acid-based, anthranilic acid-based, salicylic acid-based, cinnamic; acid-based, benzophenone-based and dibenzoylmethane-based absorbers.

Examples of the special formulation component include hormones such as estradiol, estrone, ethinylestradiol, cortisone, hydrocortisone and prednisone, vitamins such as vitamin A, vitamin B, vitamin C and vitamin E, a skin astringent such as citric acid, tartaric acid, lactic acid, aluminum chloride, potassium aluminum sulfate, allantoin chlorohydroxy aluminum, zinc p-phenolsulfonate and zinc sulfate, trichogenous accelerants such as cantharides tincture, capsicum tincture, ginger tincture, swertia extract, garlic extract, hinokitiol, carpronium chloride, glyceride pentadecanoate, vitamin E, estrogen and photosensitive elements, and whitening agents such as phosphoric acid-L-ascorbic acid magnesium and kojic acid.

EXAMPLES OF THE INVENTION

The present invention is described below in more detail with reference to examples, but it should not be construed to be limited to the examples in any way. Various methods for measurements in Examples are provided below.
[Method for Measurement of Compression Strength]

Compression strengths S10 and S30, that is, compression strengths when compressed by 10% and 30%, of a resin particle are measured by a compression test using a micro compression tester (MCTM-200) manufactured by SHIMADZU CORPORATION.

First, resin particles are placed, on a lower press plate (SKS flat plate), and a single, independent fine resin particle (no other resin particles are present in the area with a diameter of at least 100 μm) is selected using the optical microscope (×50 objective lens) of the MCTM-200. The diameter of the selected resin particle is measured using the particle size measuring cursor of the MCTM-200. Selection of a resin particle to be measured is carried out according to a target particle size for a measurement. Next, the testing indenter is lowered onto the top of the selected resin particle at a load rate provided below to apply a load, which is increased gradually up to a maximum load of 9.81 mN, to the resin particle, and then the applied load is measured when the diameter of the particle is decreased by 10% or 30% of the pre-measured diameter of the particle. Respective compression strengths are determined from measured values using the following formula. The measurements are carried out on 6 resin particles, and then the maximum value and the minimum value are excluded from the 6 compression strengths, and a mean value, of the 4 remaining compression strengths is considered as the compression strengths when compressed by 10% or 30% (S10 or S30 strength).

<Formula for Calculation of Compression Strength>

Compression Strength (MPa)=2.8×Load (N)/{π×(particle size (mm))$^2$}

<Conditions for Measurement of Compression Strength>

Testing Temperature Ambient Temperature (20° C.), Relative Humidity of 65%

Upper Press Indenter: Flat Indenter (Material: Diamond) 50 μm in Diameter

Lower Press Plate: SKS Flat Plate

Test Type: Compression Test

Test Load 9.81 mN

Load Rate: 0.732 mN/sec

[Method for Measurement of Recovery Rate]

Recovery rate of a resin particle is measured by a load-unload test using a micro compression tester (MCTM-200) manufactured by SHIMADZU CORPORATION.

First, resin particles are placed on a lower press plate (SKS flat plate), and a single, independent fine resin particle (no other resin particles are present in the area with a diameter of at least 100 μm) is selected using the optical microscope (×50 objective lens) of the MCTM-200. The diameter of the selected resin particle is measured using the particle size measuring cursor of the MCTM-200. Selection of a resin particle to be measured is carried out according to a target particle size for a measurement. Next, the testing indenter is lowered onto the top of the selected resin particle at a load rate provided below, and thus a measurement of a diameter (particle size A) when a load is applied to the particle up to a maximum test force of 9.81 mN is carried out, and subsequently a measurement of a diameter (particle size B) when the load is unloaded to a minimum test force of 1.96 mN is carried out. A respective recovery rate is determined from an amount of displacement (amount of recovery) obtained from the particle size A and the particle size B using the following formula. The measurements are carried out on 6 resin particles, and then the maximum value and the minimum value are excluded from the 6 recovery rates, and a mean value of the 4 remaining data is considered as the recovery rate.

<Formula for Calculation of Recovery Rate>

Recovery Rate (%)=Amount of Recovery (μm)/diameter (μm)×100

<Conditions for Measurement of Recovery Rate>

Testing Temperature: Ambient Temperature (20° C.), Relative Humidity of 65%

Upper Press Indenter: Flat Indenter (Material: Diamond) 50 μm in Diameter

Lower Press plate: SKS Flat Plate

Test Type: Load-unload Test

Maximum Test Force: 9.81 mN

Minimum Test Force: 1.96 mN

Load Rate: 0.732 mN/sec

Load Retention Time: 1 sec

Unload Retention Time: 1 sec

[Glass Transition Temperature of Crosslinkable Oligomer]

After a disk-shaped test piece having ϕ 10 mm and thickness of 1 mm is sandwiched between the plates at 23° C., and distance between the plates is adjusted so that normal force is 0.05 N, and then the test peace is cooled to −70° C., a measurement of glass transition temperature is started using a viscoelasticity measuring apparatus PHYSICA MCR301 (Manufactured by Anton Paar GmbH), temperature regulating system CTD450 and a liquid nitrogen feeder, analysis software Rheoplus, and grid patterned upper and lower parallel plates having ϕ 8 mm as a geometry. A maximum value of a loss tangent (tan δ) measured under the following condition is considered as a glass transition temperature: a frequency of oscillation applied to the test piece is 1 Hz, temperature-increasing rate is 5° C./min. a temperature range of the measurement is from −70° C. to 200° C., a strain is increased from 0.01% to 1% (logarithmic increase and decrease) and a normal force is 3N when the temperature is increasing within the range of from −70° C. to 50° C. and a strain is increased from 1% to 2% (logarithmic increase and decrease) and a normal force is decreased from 3N to 2N (linear increase and decrease) when the temperature is increasing in the range from 50° C. to 100° C., a measurement interval is 0.2 mM, and the atmosphere is nitrogen.

[Method for Measurement of Hysteresis Loss of Resin Formulation Used for Producing Particles]

Two fixed specimens are provided as follows: preparing a formulation liquid from the oil phase used for producing the resin particles, pouring the formulation liquid into each framework made of silicone sheets having a thickness of 6 mm, sandwiching them with PET films, further sandwiching them with glass plates, and fixing them with clips. One of the fixed specimens is subjected to a polymerization reaction at 50° C. for 24 hours and the other fixed specimen is subjected to a polymerization reaction at 90° C. for 8 hours to provide 2 types of resin sheets having a thickness of 6 mm and 2 mm, respectively, as samples for measuring physical properties of the resin formulation used for producing the resin particles.

Square plate-shaped resin sheets (plane size of 12 mm×12 mm) are cut out from the resin sheet having a thickness of 6 mm obtained in Examples or Comparative Examples, and the resultant square plate-shaped resin sheets are used as test pieces.

Under conditions and circumstances for a measurement shown below, the test piece is compressed at a compression rate of 10 mm/min using a compression tester to compress the thickness of the test piece by 30%, and then decompressed at the same rate as that of the compression until the initial thickness is recovered, and thus changes in load and strain during a time period between the beginning of the compression and completion of the decompression to recover the initial thickness are measured. Measurement of each of these values is carried out on 3 test pieces, and a mean value of the 3 measurements is adopted as the final measurement value.

The test piece is acclimated to ambient conditions under the standard atmosphere of condition 23/50 (temperature of 23° C. and relative humidity of 50%), Grade 2 of JIS K 7100:1999 for 16 hours, and a measurement is carried out under the same standard atmosphere. An initial thickness of the test piece is measured as a thickness of the test piece when the test piece is subjected to a load (initial load) of 0.5 N (stress of 3.5 kPa). A displacement of the test piece is measured based on a position of a press plate (movable plate) jig when the test piece is subjected to a load (initial load) of 0.5N (stress of 3.5 kPa) as the origin.

<Conditions for Measurement>

Compression Tester: TENSILON Universal Testing Instrument "UCT-10T" (manufactured by ORIENTEC CORPORATION)

Data Processing Software: Cycle Test Mode "UTPS-458C" (manufactured by Soft Brain Co. Ltd.)

Compressing Jig: Compressing Jig according to JIS K 6767:1999

<Method for Calculation of Hysteresis Loss>

Hysteresis energy and a hysteresis loss in, the first cycle are calculated from pressurizing energy (J) and depressurizing energy (J) in the first cycle using the following formula.

Hysteresis Energy (J)=Pressurizing Energy (J)−Depressurizing Energy (J)

A hysteresis loss (%)=100×(Hysteresis Energy (J)/Pressurizing Energy (J)

[Method for Measurement of Volumetric Average Diameter of Resin Particles]

A volumetric average diameter (an arithmetic average diameter of a volumetric particle size distribution) of resin particles is measured by the following method using Coulter Multisizer II (a measuring apparatus manufactured by Beckman Coulter KK). In the measurement, the measurement is carried out with calibration using 50 μm aperture according to Reference MANUAL FOR THE COULTER MULTISIZER (1987) issued by Coulter Electronics Limited.

Specifically, 0.1 g of resin particles are preliminary dispersed in 10 ml of a nonionic surfactant (0.1 wt %) using a touch mixer (manufactured by Yamato Scientific Co., Ltd. "TOUCH MIXER MT-31") and an ultrasonication cleaner (manufactured by VELVO-CLEAR "ULTRASONIC CLEANER VS-150") to obtain a fluid dispersion. Subsequently, in the beaker filled with ISOTON (registered trademark) II (electrolyte solution for measurement manufactured by Beckman Coulter KK) installed in the main part of the Coulter Multisizer II, the above-described fluid dispersion is added dropwise with a spuit (syringe) under gentle agitation so that the concentration meter in the display of the main part of Coulter Multisizer II shows a reading of about 10%. Then, the following parameters are entered to the main part of Coulter Multisizer II: Aperture Size (Diameter)=100 μm, Current (Aperture Electrode)=1600 μA, Gain (Gain)=2, and Polarity (Polarity of Internal Electrode)=+for Example 7 and then measurement is carried out manually (manual operation mode), and Aperture Size (Diameter)=50 μm, Current (Aperture Electrode)=800 μA, Gain (Gain)=4, Polarity (Polarity of Internal Electrode)=+for the other Examples and Comparative Examples, and then, measurement is carried out manually (manual operation mode). During the measurement, the liquid in the beaker is gently agitated to the extent that no bubble is included, and the measurement is terminated when measurements of one hundred thousand resin particles are completed. An arithmetic average diameter of a volumetric particle size distribution of one hundred thousand resin particles is considered as a volumetric average diameter.

Crosslinkable Oligomer

Synthesis Example 1

A flask was loaded with 1400 g (1 mole) of hexamethylene diisocyanate allophanate adduct of 1,6-hexanediol polycarbonate diol (NCO content of 13.5%, tetra functional), 1.4 g of hydroquinone monomethyl ether and 1265 g (5.5 mole) of caprolactone 1 mole adduct of 2-hydroxyethyl acrylate (molecular weight of 230), and then a reaction was carried out at 70 to 80° C. until an amount of free isocyanate reached 0.1% or less to obtain crosslinkable oligomer A ((meth)acrylic equivalent of 485 g/mol). The (meth)acrylic equivalent was calculated using a calculation formula: (1400+1265)/5.5=485.

With 100 parts by mass of the crosslinkable oligomer A, 1 parts by mass of 2,2-azobis(2,4-dimethylvaleronitrile) (hereinafter abbreviated as "AVNV") (manufactured by JAPAN FINECHEM COMPANY, INC.) was compounded, and then was dissolved. The resultant was applied on a polyethylene terephthalate base material (PET manufactured by Toray Industries, Inc., product number: #100 T60), and sandwiched with a silicone packing to provide a film thickness of about 1 mm, and then heated in an oven at 50° C. for 24 hours to cure. The glass transition temperature of the obtained cured product A was 18° C.

Synthesis Example 2

A flask was loaded with 1340 g (1 mole) of a hexamethylene diisocyanate adduct of an ethylene oxide adduct of trimethylolpropane (NCO content of 9.4%, tri functional on average), 0.8 g of hydroquinone monomethyl ether and 365 g (3.15 mole) of 2-hydroxyethyl acrylate (molecular weight of 116), and then a reaction was carried out at 70 to 80° C. until an amount of free isocyanate reached 0.1% or less to obtain a crosslinkable oligomer B ((meth)acrylic equivalent of 541 g/mol). The glass transition temperature of the cured product B derived from the crosslinkable oligomer B was 8° C.

High-Recoverability Resin Particle

Example 1

Fifty (50) parts by mass of n-butyl acrylate as a (meth)acrylic acid ester based monofunctional monomer, 50 parts by mass of the crosslinkable oligomer A obtained in Synthesis Example 1 and 0.1 parts by mass of "KAYAMER (registered trademark) PM-21" (manufactured by Nippon Kayaku Co., Ltd.) as an oil-soluble surfactant were mixed with 0.5 parts by mass of AVNV (manufactured by JAPAN FINECHEM COMPANY, INC) and 0.1 parts by mass of benzoyl peroxide as polymerization initiators to adjust an oil phase. Further, 200 parts by mass of deionized water as an aqueous medium was mixed with 6.1 parts by mass of magnesium pyrophosphate as a dispersant produced by double decomposition process to adjust an aqueous phase.

Then, the above oil phase was dispersed in the above aqueous phase using a TK-homomixer (manufactured by PRIMIX Corporation) at 8000 rpm for 5 minutes to obtain a fluid dispersion of about 8 μm. Subsequently, a polymerization vessel equipped with an agitator and a thermometer was loaded with the fluid dispersion, an internal temperature of the polymerization vessel was elevated to 50° C. and agitation of the above suspension was continued for 3 hours, and 0.05 parts by mass of sodium dodecylbenzenesulfonate as a surfactant was added to the above suspension, and then the internal temperature of the polymerization vessel was elevated to 90° C. (second elevation of temperature) and the above suspension was agitated at 90° C. for 3 hours to complete a suspension polymerization reaction.

The above suspension was cooled, and then the dispersant (magnesium pyrophosphate) contained in the suspension was decomposed by hydrochloric acid. Subsequently, the suspension was dewatered by filtration to separate solid content, and the solid content was washed with sufficient amount of water. To the washed solid content was added 2.5 parts by mass of a hydrophobic colloidal silica (manufactured by NIPPON AEROSIL CO., LTD., trade name "AEROSIL (registered trademark) R974") as an inorganic powder, and vacuum dried at 50° C. for 24 hours. The resin particles aggregated during drying was cracked using a crusher "Labo Millser" (product number: LM-PLUS) manufactured by Osaka Chemical Co., Ltd. to obtain dried and cracked resin particles. Then, by sieving through 63 μm opening mesh, resin particles having a particle size not less than an upper limit (63 μm) was eliminated (cut) to obtain resin particles having a volumetric mean particle size of 8.3 μm. The resin particles had a 30% compression strength of 2.31 and a recovery rate of 33.1%. Further, a resin constituting the resin particles had a hysteresis loss of 15%.

Example 2

Resin, particles having a volumetric mean particle size of 7.5 μm were obtained in the same way as Example 1 except that the crosslinkable oligomer B obtained in Synthesis Example 2 was used instead of the crosslinkable oligomer A. The resin particles had a 30% compression strength of 4.9 and a recovery rate of 25.4%. Further, a resin constituting the resin particles had a hysteresis loss of 13%.

Example 3

Resin particles having a volumetric mean particle size of 7.8 μm were obtained in the same way as Example 1 except that n-butyl acrylate used was 70 parts by mass and a crosslinkable oligomer A used was 30 parts by mass. The resin particles had a 30% compression strength of 3.3 and a recovery rate of 22.5%. Further, a resin constituting the resin particles had a hysteresis loss of 22%.

Example 4

Resin particles having a volumetric mean particle size of 9.2 μm were obtained in the same way as Example 1 except that n-butyl acrylate used was 30 parts by mass and a crosslinkable oligomer A used was 70 parts by mass. The resin particles had a 30% compression strength of 3.8 and a recovery rate of 27.5%. Further, a resin constituting the resin particles had a hysteresis loss of 17%.

Example 5

Resin, particles having a volumetric mean particle size of 8.5 μm were obtained in the same way as Example 1 except that 30 parts by mass of n-butyl acrylate, 10 parts by mass of 2-ethylhexyl acrylate and 10 parts by mass of butyl methacrylate were used as (meth)acrylic acid ester-based monofunctional monomers. The resin particles had a 30% compression strength of 3.5 and a recovery rate of 30.3%. Further, a resin constituting the resin particles had a hysteresis loss of 18%.

Comparative Example 1

Resin particles having a volumetric mean particle size of 8.9 μm were obtained in the same way as Example 1 except that a commercially available urethane (meth)acrylate, trade name: Shiloh Grade: UV-7000B (Tg=52° C., functional groups=2.5) manufactured by The Nippon Synthetic Chemical Industry Co., Ltd., was used instead of the crosslinkable oligomer A. The resin particles had a 30% compression strength of 7.21 and a recovery rate of 17.8%. Further, a resin constituting the resin particles had a hysteresis loss of 15%.

Comparative Example 2

Resin particles having a volumetric mean particle size of 9.1 μm were obtained in the same way as Example 1 except that a commercially available urethane (meth)acrylate, UV-3200B (Tg=−8° C., functional groups=2) manufactured by The Nippon Synthetic Chemical Industry Co., Ltd., was used instead of the crosslinkable oligomer A. The resin particles had a 30% compression strength of 8.31 and a recovery rate of 18.9%. The obtained resin particles had stickiness. Further, a resin constituting the resin particles had a hysteresis loss of 20%.

Comparative Example 3

Resin particles having a volumetric mean particle size of 8.3 μm were obtained in the same way as Example 1 except that n-butyl acrylate used was 80 parts by mass and 20 parts, by mass of trimethylolpropane trimethacrylate (Tg>250° C.) was used instead of the crosslinkable oligomer A. The resin particles had a 30% compression strength of 1.49 and a recovery rate of 19.1%. Further, a resin constituting the resin particles had a hysteresis loss of 45%.

Comparative Example 4

Resin particles having volumetric mean particle size of 8.8 μm were obtained in the same way as Example 1 except that n-butyl acrylate used was 80 parts by mass and 20 parts by mass of polyethylene glycol dimethacrylate (n (ethylene glycol repeat)=14, Tg=−23° C., functional groups=2) was used instead of the crosslinkable oligomer A. The resin particles had a 30% compression strength of 10.86 and a recovery rate of 14.1%. The obtained resin particles had stickiness. Further, a resin constituting the resin particles had a hysteresis loss of 50%.

Example 6 (Example Regarding Small Particle Size)

Resin particles having a volumetric particle size of 3.5 μm were obtained in the same way as Example 1 except that an oil phase and an aqueous phase were mixed and dispersed using a homomixer to obtain a fluid dispersion, and the fluid dispersion was passed once through a microfluidizer (HG-5000, manufactured by MIZUHO INDUSTRIAL CO., LTD) under a pressure of 100 kg/cm$^2$. The resin particles showed a 30% compression strength of 4.5 and a recovery rate of 24.5%. Further, a 10% compression strength was 0.51 and a hysteresis loss of the resin was 15.

Example 7 (Example Regarding Large Particle Size)

The resin particles having a volumetric mean particle size of 25.1 μm were obtained in the same way as Example 2 except that rotation rate of the TK homomixer was 1500 rpm. Resin particles showed a 30% compression strength of 1.8 and a recovery rate of 37.5%. Further, a 10% compression strength was 0.13 and a hysteresis loss of the resin was 13.

Raw materials used for producing particles and physical properties of the resin particles are summarized in Table 1.

TABLE 1

|  |  |  | Example | | | | | | | Comparative Example | | | |
|---|---|---|---|---|---|---|---|---|---|---|---|---|---|
|  |  |  | 1 | 2 | 3 | 4 | 5 | 6 | 7 | 1 | 2 | 3 | 4 |
| resin formulation | (meth) acrylate | butyl acrylate | 50 | 50 | 70 | 30 | 30 | 50 | 50 | 50 | 50 | 80 | 80 |
|  |  | 2-ethylhexyl acrylate | — | — | — | — | 10 | — | — | — | — | — | — |
|  |  | butyl methacrylate | — | — | — | — | 10 | — | — | — | — | — | — |
|  | crosslinkable oligomer | crosslinkable oligomer A | 50 | — | 30 | — | 50 | 50 | — | — | — | — | — |
|  |  | crosslinkable oligomer B | — | 50 | — | 70 | — | — | 50 | — | — | — | — |
|  |  | UV-7000B | — | — | — | — | — | — | — | 50 | — | — | — |
|  |  | UV-3200B | — | — | — | — | — | — | — | — | 50 | — | — |
| polyfunctional (meth)acrylate |  | trimethylolpropane trimethacrylate | — | — | — | — | — | — | — | — | — | 20 | — |
|  |  | polyethylene glycol dimethacrylate | — | — | — | — | — | — | — | — | — | — | 20 |
| polymerization initiator |  | AVNV | 0.5 | 0.5 | 0.5 | 0.5 | 0.5 | 0.5 | 0.5 | 0.5 | 0.5 | 0.5 | 0.5 |
| resin property |  | hysteresis loss (%) | 15 | 13 | 22 | 17 | 18 | 15 | 13 | 15 | 20 | 45 | 50 |
| particle property |  | volumetric average diameter (μm) | 8.3 | 7.5 | 7.8 | 9.2 | 8.5 | 3.5 | 25.1 | 8.9 | 9.1 | 8.3 | 8.8 |
|  |  | S10(N/mm) | 0.36 | 0.36 | 0.36 | 0.36 | 0.37 | 0.51 | 0.13 | 0.36 | 0.37 | 0.51 | 0.41 |
|  |  | S30(N/mm) | 2.31 | 4.9 | 3.3 | 3.8 | 3.5 | 4.5 | 1.8 | 7.21 | 8.31 | 1.49 | 10.86 |
|  |  | S30/S10 | 6.4 | 13.6 | 9.2 | 10.6 | 9.5 | 8.8 | 13.8 | 20.0 | 22.5 | 2.9 | 26.5 |
|  |  | recovery rate (%) | 33.1 | 25.4 | 22.5 | 27.5 | 30.3 | 24.5 | 37.5 | 17.8 | 18.9 | 19.1 | 14.1 |

Coating Composition

Example 8 and Comparative Example 5

With each 0.8 g of resin particles obtained in above-described Example 1 to 5 and Comparative Examples 1 to 4, 6 of a binder resin (RST-201 manufactured by DKS Co. Ltd.), 0.15 g of a photopolymerization initiator (Daroeur 1173 manufactured by BASF) and 4 g of toluene as a solvent were compounded to obtain a coating composition. Coating compositions containing resin particles obtained in Example 1 to 5 are collectively referred to as Example 8 and coating compositions containing resin particles obtained in Comparative Examples 1 to 4 are collectively referred to as Comparative Example 5. These coating compositions were applied on ABS plates using a 45 μm applicator, dried, and then cured by irradiation of ultraviolet rays to obtain coating films. Recoverability was evaluated by using the obtained coating film.

A coating film was brushed with a brass brush by reciprocating motion for 10 times, and then recoverability was classified as Grade A(O) when almost no scratch remains, Grade B(Δ) when a slight white scratch remains, or Grade C(X) when a white scratch remains.

Recoverability of all of the coating films containing resin particles of Example 1 to 5 was Grade A, recoverability of all of the coating films containing resin particles of Comparative Examples 1 and 2 was Grade B, and recoverability of all of the coating films containing resin particles of Comparative Examples 3 and 4 was Grade C.

Formulation Example of Cosmetics

Formulation Example 1

Production of Power Foundations

| Amount in formulation | |
|---|---|
| Resin particles obtained in Example 1 | 10.0 parts by mass |
| Red iron oxide | 3.0 parts by mass |
| Yellow iron oxide | 2.5 parts by mass |
| Black iron oxide | 0.5 parts by mass |
| Titanium oxide | 10.0 parts by mass |
| Mica | 20.0 parts by mass |

-continued

| Amount in formulation | |
|---|---|
| Talc | 44.0 parts by mass |
| Liquid paraffin | 5.0 parts by mass |
| Octyldodecyl myristate | 2.5 parts by mass |
| Petrolatum | 2.5 parts by mass |
| Antiseptic | proper amount |
| Flavoring | proper amount |

Method for Production

Resin particles, red iron oxide, yellow iron oxide, black iron oxide, titanium oxide, mica and talc are mixed using a Henschel mixer to provide a mixture. A liquid paraffin, octyldodecyl myristate, petrolatum and an antiseptic are mixed and dissolved, and the obtained solution is added to the above mixture, and then the resultant is mixed homogeneously. A flavoring is added to the homogeneous mixture, and the resultant is mixed, and then pulverized and passed through a sieve. The resultant is shaped by compression using a metal tray to provide a powder foundation.

Formulation Example 2

Production of Makeup Milky Lotion

| Amount in formulation | |
|---|---|
| Resin particles obtained in Example 1 | 10.0 parts by mass |
| Stearic acid | 2.5 parts by mass |
| Cetyl alcohol | 1.5 parts by mass |
| Petrolatum | 5.0 parts by mass |
| Liquid paraffin | 10.0 parts by mass |
| Polyethylene(10 mole)monooleic acid ester | 2.0 parts by mass |
| Polyethylene glycol 1500 | 3.0 parts by mass |
| Triethanol amines | 1.0 parts by mass |
| Purified water | 64.5 parts by mass |
| Flavoring | 0.5 parts by mass |
| Antiseptic | proper amount |

Method for Production

First, stearic acid, cetyl alcohol, petrolatum, a liquid paraffin and polyethylene mono oleic acid ester are heated and dissolved to provide a solution. Then, to the solution, a resin particle is added and mixed, and the resultant is maintained at 70° C. (an oil phase). Next, polyethylene glycol and triethanol amines are added to purified water, and heated and dissolved, and the resultant is maintained at 70° C. (an aqueous phase). The oil phase is added to the aqueous phase, and preliminary emulsification is carried out, and then the resultant is emulsified homogeneously using a homomixer, and after the emulsification the emulsion is cooled to 30° C. with stirring to provide a makeup milky lotion.

What is claimed is:

1. A high-recoverability resin particles having a mean particle size of 1 to 100 μm containing a cross-linked (meth)acrylic acid ester-based resin, wherein the high-recoverability resin particles have a recovery rate of 22% or greater, and a 30% compression strength of 1.5 to 5.0 kgf/mm$^2$,
wherein the cross-linked (meth)acrylic acid ester-based resin contains a resin derived from a crosslinkable oligomer having two or more radical-polymerizable groups obtained by reacting (a) polyol, (b) polyisocyanate and (c) (meth)acrylic acid esters having an OH group, and a (meth)acrylic acid ester-based monofunctional monomer.

2. The high-recoverability resin particles according to claim 1, wherein the cross-linked (meth)acrylic acid ester-based resin shows Tg of 0 to 30° C. (determined from viscoelasticity) when the crosslinkable oligomer is cured alone.

3. The high-recoverability resin particles according to claim 1, wherein the cross-linked (meth)acrylic acid ester-based resin is a polymerization product of a monomer mixture obtained by polymerization of the monomer mixture containing 20 to 80 mass % of a (meth)acrylic acid ester-based monofunctional monomer and 80 to 20 mass % of a crosslinkable oligomer, wherein the (meth)acrylic acid ester-based monofunctional monomer is a (meth)acrylic acid ester of an alcohol having 1 to 8 carbon atoms.

4. The high-recoverability resin particles according to claim 1, wherein the cross-linked (meth)acrylic acid ester-based resin contains of a resin formulation showing a hysteresis loss of 30% or less.

5. The high-recoverability resin particles according to claim 1, wherein the crosslinkable oligomer shows an acrylic equivalent of 300 to 1000 g/mol.

6. The high-recoverability resin particles according to claim 1, wherein the polyol is selected from a polyester-based polyol, a polyether-based polyol, a polycarbonate polyol, an aliphatic hydrocarbon-based polyol and an alicyclic hydrocarbon-based polyol.

7. The high-recoverability resin particles according to claim 1, wherein the polyisocyanate is selected from an aliphatic polyisocyanate, an alicyclic polyisocyanate, an aromatic polyisocyanate and an aromatic-aliphatic polyisocyanate.

8. The high-recoverability resin particles according to claim 1, wherein the (meth)acrylic acid ester having OH group is selected from 2-hydroxyethyl acrylate, 2-hydroxyethyl methacrylate, 2-hydroxy propyl acrylate, 2-hydroxy propyl methacrylate, 4-hydroxy butyl acrylate, caprolactone modified-2-hydroxyethyl acrylate, polyethylene glycol mono(meth)acrylic acid ester, polypropylene glycol monoacrylic acid ester, polybutylene glycol mono(meth)acrylic acid ester, 2-(meth)acryloyloxyethyl-2-hydroxyethyl phthalate, phenylglycidyl ether (meth)acrylate, pentaerythritol triacrylate, dipentaerythritol pentaacrylate and caprolactone-modified dipentaerythritol penta(meth)acrylate.

9. A coating composition containing the high-recoverability resin particles according to claim 1.

10. A coating film obtained by applying and drying the coating composition according to claim 9.

11. A cosmetics containing the high-recoverability resin particles according to claim 1.

* * * * *